United States Patent
Schub

(10) Patent No.: US 11,382,637 B1
(45) Date of Patent: Jul. 12, 2022

(54) COMBINATION SURGICAL DRILL AND REMOTE GRASPING DEVICE

(71) Applicant: David Schub, Rancho Santa Fe, CA (US)

(72) Inventor: David Schub, Rancho Santa Fe, CA (US)

(73) Assignee: Schrilla, LLC, Rancho Santa Fe, CA (US)

( * ) Notice: Subject to any disclaimer, the term of this patent is extended or adjusted under 35 U.S.C. 154(b) by 0 days.

(21) Appl. No.: 17/229,771

(22) Filed: Apr. 13, 2021

(51) Int. Cl.
*A61B 17/16* (2006.01)

(52) U.S. Cl.
CPC ...... *A61B 17/1615* (2013.01); *A61B 17/1631* (2013.01)

(58) Field of Classification Search
CPC . A61B 17/16; A61B 17/1613; A61B 17/1615; A61B 17/1617; A61B 17/162; A61B 17/1624; A61B 17/1626; A61B 17/1628; A61B 17/1631
See application file for complete search history.

(56) References Cited

U.S. PATENT DOCUMENTS

| | | | |
|---|---|---|---|
| 5,681,333 A * | 10/1997 | Burkhart | A61B 17/1778 606/104 |
| 10,765,420 B2 * | 9/2020 | Lunn | A61B 17/06004 |
| 10,792,052 B2 * | 10/2020 | Acevedo | A61B 17/1682 |
| 11,234,714 B2 * | 2/2022 | Schub | A61B 17/29 |
| 2004/0243135 A1 * | 12/2004 | Koseki | A61B 17/8861 606/80 |
| 2016/0151076 A1 * | 6/2016 | Bake | A61F 2/4684 606/80 |
| 2021/0106343 A1 * | 4/2021 | Schub | A61B 17/1617 |

* cited by examiner

*Primary Examiner* — Eric S Gibson
(74) *Attorney, Agent, or Firm* — Justin Lampel

(57) ABSTRACT

A surgical instrument is provided. The surgical instrument has a drill bit employable in drilling procedures wherein the drill bit has an internal grasping hook. As a result, the drill bit may not only drill into bone, but may also be used to grasp an object within or part of the body. The present surgical instrument reduces contamination and difficulty which may otherwise result from switching surgical instruments from a drill to a grasping mechanism or from the need to drill multiple holes into the patient's body.

10 Claims, 4 Drawing Sheets

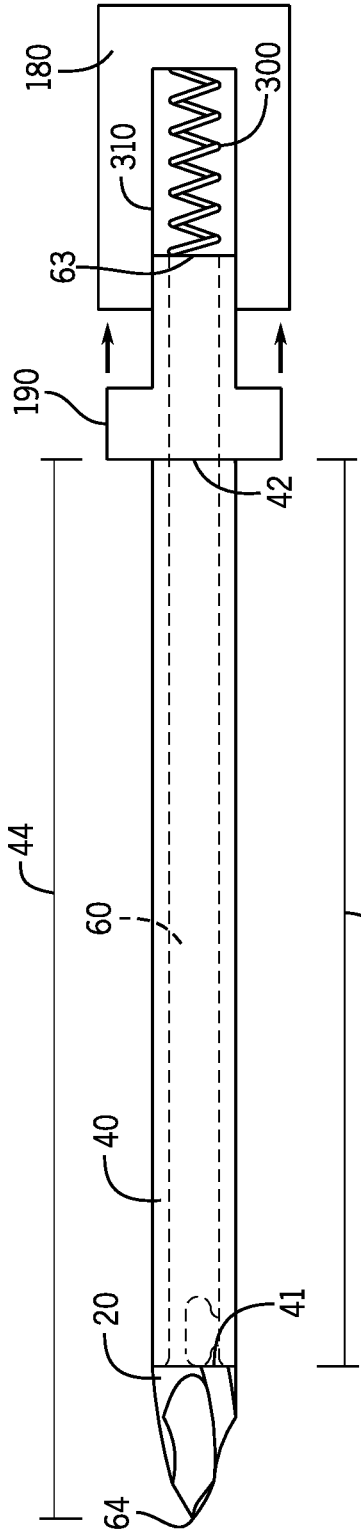
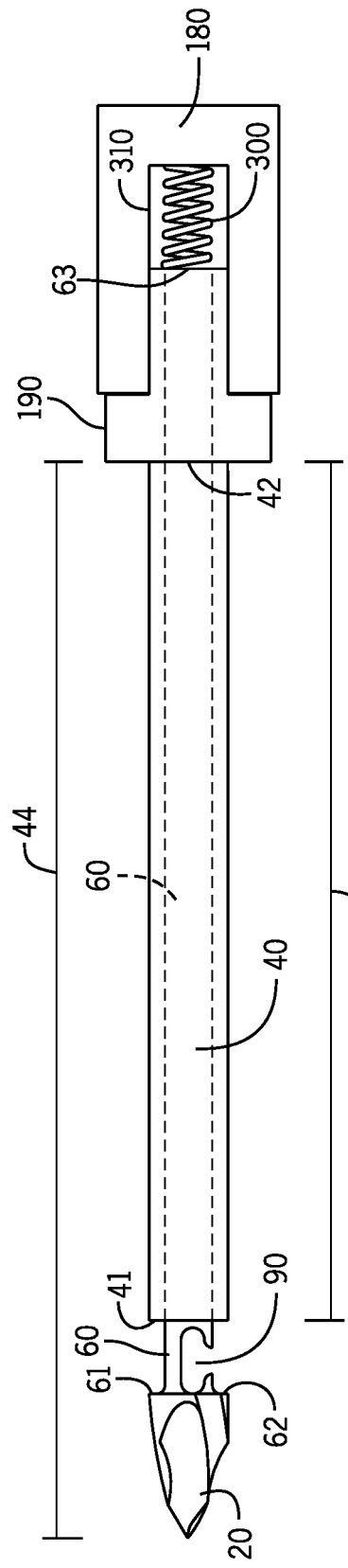

COMBINATION SURGICAL DRILL AND REMOTE GRASPING DEVICE

BACKGROUND OF THE INVENTION

A surgical instrument is provided. The surgical instrument has a drill bit employable in drilling procedures wherein the drill bit has an internal grasping hook. As a result, the drill bit may not only drill into bone, but may also be used to grasp an object within or part of the body. The present surgical instrument reduces contamination and difficulty which may otherwise result from switching surgical instruments from a drill to a grasping mechanism or from the need to drill multiple holes into the patient's body.

During the performance of surgical procedures, there are often situations which require that a tunnel be drilled through, for example, a patient's bone to allow access to another compartment or space within the body, such as a joint space. This is something which is commonly encountered in arthroscopic surgery in orthopedics. In these procedures, there are generally small incisions made in the patient's skin to access spaces within the body that are in need of repair.

During such procedures, the surgeon will frequently drill a passage which communicates completely through a bone structure of the patient, and in a subsequent surgical step, the surgeon will frequently employ secondary instruments to feed a required component through the passage previously formed by the drill.

This conventional mode of drilling and subsequent feeding of a secondary component through the formed passage, currently requires that a surgical drill be communicated through one body entry point on the patient. To complete the task of feeding a part or component through the drilled passage, the surgeon must then either remove the drill from its entry point in the patient and insert a secondary instrument for grasping, in order to feed a secondary component through the formed passage, or the surgeon must form a secondary entry point into the body of the patient for positioning of the grasping instrument.

Both options required multiple actions by a skilled surgeon extending the duration of the surgical procedure. Further, forming multiple passages into the body of the patient is less than desirable and potentially increases recovery time and risk of infection due to the formation of such multiple access points.

The forgoing examples of related art in the field of orthopaedic surgery and limitations related therewith are intended to be illustrative and not exclusive, and they do not imply any limitations on the presently described combination surgical drill and remote grasping device. Various limitations of the related art will become apparent to those skilled in the art upon a reading and understanding of the specification below and the accompanying drawings.

The present device may also be used in non-orthopedic surgeries and even in non-medical procures as diverse as, for example, automotive repair.

SUMMARY OF THE INVENTION

A surgical instrument is provided. The surgical instrument has a drill bit employable in drilling procedures wherein the drill bit has an internal grasping hook. As a result, the drill bit may not only drill into bone, but may also be used to grasp an object within or part of the body. The present surgical instrument reduces contamination and difficulty which may otherwise result from switching surgical instruments from a drill to a grasping mechanism or from the need to drill multiple holes into the patient's body.

The combination drill and grasping instrument system herein disclosed and described provides a solution to the shortcomings in prior art noted above. It achieves the above noted goals through the provision of a surgical drill configured while the instrument is in a closed configuration, to form openings and passages in the bones of a patient in a conventional fashion. The drill portion of the device is additionally configured during operative control by the surgeon to form a grasping tool which may grasp an object within or part of the body. Thus, the combination drill and grasping device herein is employable, for example, by a surgeon in a first step to drill through and form a passage through bone. Subsequent to completion of the first step, with the drill bit communicating through a distal end of the passage, in a second step, the surgeon can operate the internal grasping hook cut-out portion which may grasp and pull an object or component backwards through the hole just formed by the drill.

By configuring the device herein in a manner enabling its employment for two tasks during a surgery, multiple entry points into a patient for surgery can be reduced or eliminated, thus making the procedure itself less trying upon the patient. Further, in instances where a component must be pulled back through a previously drilled hole, the present instrument saves significant time for the surgeon, since he/she no longer must employ a secondary grasping instrument to "fish" for the component after feeding that instrument through the drilled hole.

With respect to the above description, before explaining at least one preferred embodiment of the herein disclosed combination drill and grasping instrument in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based, may readily be utilized as a basis for designing and configuring other drill and grasping instruments employed for surgery (or even outside of surgery), and for carrying out the several purposes of the presently disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Finally, unless provided with a specific different respective definition, the term "substantially" herein, means plus or minus five percent. It is an object of this invention to provide a surgical instrument configured for both drilling and for grasping. It is a further objection of the invention to provide such a device which will shorten surgery times and lessen the physical impact on patients by reducing the number of body entry points and steps required during surgery. These and other objects of the combination surgical drill and grasping instrument herein, will be brought out in the following part of the specification, wherein detailed description is for the purpose of fully disclosing the invention without placing limitations thereon.

BRIEF DESCRIPTION OF DRAWING FIGURES

The accompanying drawings, which are incorporated herein and form a part of the specification, illustrate some, but not the only or exclusive, examples of embodiments and/or features of the surgical instrument. It is intended that the embodiments and figures disclosed herein are to be considered illustrative rather than limiting.

FIG. 8 illustrates the entire instrument in the closed orientation.

FIG. 9 illustrates the entire instrument in the open orientation.

DETAILED DESCRIPTION OF THE PREFERRED EMBODIMENTS OF THE INVENTION

Figure 1:
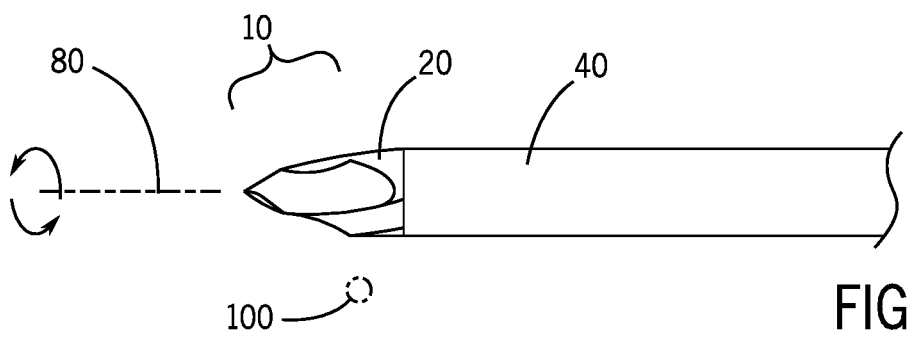
FIG. 1 depicts a side view of the combination drill bit and grasping instrument in one embodiment, showing the drill bit in a closed (or "collapsed") orientation.

A surgical instrument is provided. The surgical instrument has a drill bit employable in drilling procedures wherein the drill bit has an internal grasping hook. As a result, the drill bit may not only drill into bone, but may also be used to grasp an object within or part of the body. The present surgical instrument reduces contamination and difficulty which may otherwise result from switching surgical instruments from a drill to a grasping mechanism or from the need to drill multiple holes into the patient's body.

In this description, the directional prepositions of up, upwardly, down, downwardly, front, back, top, upper, bottom, lower, left, right and other such terms refer to the device as it is oriented and appears in the drawings and are used for convenience only. They are not intended to be limiting or to imply that the device has to be used or positioned in any particular orientation.

Referring now to the figures, in an embodiment, a side view of the surgical instrument 10 is provided. The surgical instrument 10 may be a drill bit having a head portion 20 and a body portion 40. The body 40 may have a first end 41 and a second end 42. The surgical instrument 10 may be made of, for example, metal, rubber and/or plastic components. Preferably, the surgical instrument 10 is durable, resistant to corrosion and is easily sterilizable for repeat usage.

In an embodiment, the body portion 40 may move with respect to the stationary head portion 20 (which may rotate during the drilling process). In one embodiment, the body portion 40 may be flexible whereas the head portion 20 is rigid. The body portion 40 may be a flexible sheath which may be compressed. In particular, the body portion 40 (or "sheath") may be pulled back and may move away from the head portion 20 from a first orientation (as shown in FIG. 8) to a second orientation (as shown in FIG. 9). In the first orientation, the head portion 20 of the drill bit may rotate three hundred and sixty degrees along an axis 80 in unison with the body portion 40 so that the head portion 20 (and potentially body portion 40 as well) may be used to drill into, for example, bone of a person's body during surgery. In the first orientation (the "closed" orientation of FIGS. 1 and 5) the instrument therefore acts as a standard surgical drill. In the second orientation of FIGS. 2-4 (the "open" orientation) the instrument may be used to grasp an object 100. In the open orientation of FIGS. 2, 3, 4 and 9 the drill bit 20 (and preferably the entire device 1) is prevented from rotating by a mechanical lock (not shown). The drill bot 20 may also be prevented from rotated when the device 1 is grasping an object 100 in the squeezed orientation of FIG. 10. In particular, the drill bit 20 may only rotate if the body 40 portion completely covers the cut-out portion 90.

Figure 6:
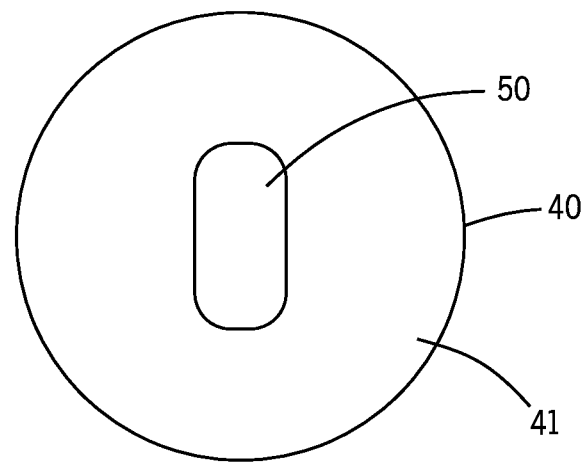
FIG. 6 illustrates a sectional view of the body of the drill bit showing the internal channel.
Figure 7:
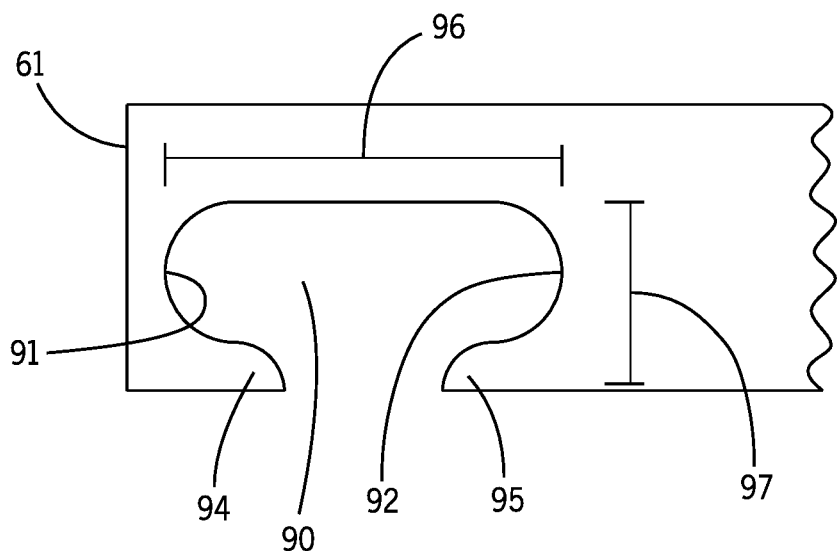
FIG. 7 illustrates a detailed view of the grasping section of the shaft of the drill bit head.

In an embodiment, the body portion 40 may have an interior channel 50 (FIG. 6) that receives the shaft 60. The shaft 60 is permanently secured to the drill bit head 20. The shaft 60 is connected to a motor (not shown) which operates the shaft 60 and allows the instrument 10 to act as a drill.

The shaft 60 may have a first end 61 which is part of, or permanently connected to, a back 62 of the drill bit head 20. The shaft 60 may further have a second end 63 (FIG. 8) which is secured near a handle 180 of the instrument; wherein the handle 180 has an activation trigger 190. The distal end 64 of the head portion 20 remains at a constant distance from the handle 180 of the instrument 10. More specifically, the distance 44 (FIG. 8) between the distal end 64 of the head portion 20 to the handle 180 remains constant.

The body portion 40 of the instrument may have a first end 41 (FIG. 8) and a second end 42 wherein the distance between the first end 41 and the second end 42 of the body portion 40 defines a length 43.

Figure 4:
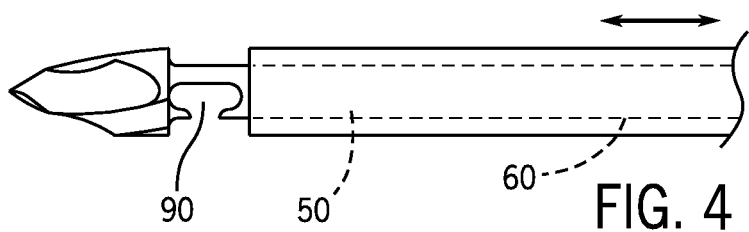
FIG. 4 depicts a side view of the combination drill bit and grasping instrument in one embodiment, showing the interior of the drill bit in the open orientation.

The shaft 60 of the head 20 may have a cut-out portion 90 (FIG. 4). The cut-out portion 90 is illustrated as generally oval, having rounded edges. In the preferred embodiment, the cut-out portion 90 is oval; however, various other shapes may be implemented. The cut-out portion 90 may have a first end 91 located near the drill bit head 20 and a second end 92. The first end 91 of the cut-out portion may have an extended lip 94 and the second end 92 of the cut-out portion may have an extended lip 95. The cut-out portion 90 may further have a length 96 and a width 97. In an embodiment, the cut-out portion 90 is completely sealed when the body 40 is adjacent to the drill bit head 20.

Figure 2:
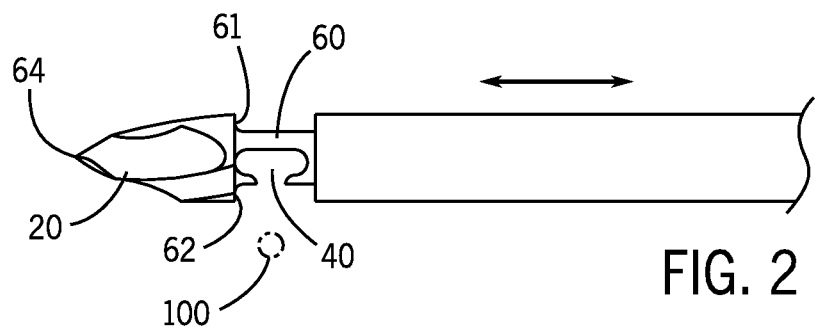
FIG. 2 depicts a side view of the combination drill bit and grasping instrument in one embodiment, showing the drill bit in the open (or "expanded") orientation wherein the instrument may be used to grasp an object or portion of a person's body.
Figure 3:
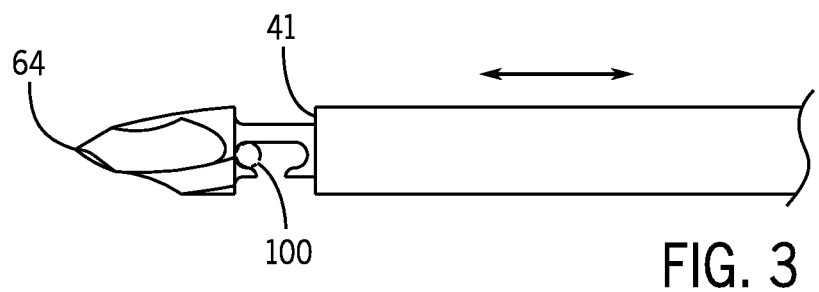
FIG. 3 depicts a side view of the combination drill bit and grasping instrument in one embodiment, showing the drill bit grasping a suture.

When the drill bit head 20 is in the open orientation of FIG. 2, the extended lips 94, 95 of the cut-out portion 90 may allow a surgeon to grasp an object 100 (See FIG. 3), such as a vein, artery, muscle, suture, or other tissue or other non-organic object during a medical procedure. Once the object 100 is fully or partially within the interior of the cut-out portion 90 the surgeon may release the trigger 190 (attached to a spring) to allow the body portion 40 to return to its relaxed state of FIGS. 1 and 5. When the object 100 is located fully or partially within the interior of the cut-out portion 90 and the body portion 40 is returned to its relaxed state of FIGS. 1 and 5 (the closed orientation), the object 100 may become grasped or squeezed between the first end 91 of the cut-out portion 90 of the head portion 20 and the first end 41 of the body portion 40 of the surgical instrument 10. Once grasped, the surgeon may move, remove or otherwise adjust the object 100 per the surgeon's needs. The surgeon may also elect to use the cut-out portion 90 to grasp and move the object 100 without releasing the trigger 190 to force the body portion 40 back toward the closed orientation to squeeze the object 100.

If the surgeon wishes to remove the object 100 from the body, the surgeon will make the cut-out portion 90 grasp the object 100 while the object 100 is pulled from the body. If the surgeon wishes to merely adjust the location of the object 100, the surgeon will release the object 100 once the object 100 is repositioned by pushing the drill bit head 20 forward toward the open position so that the object 100 may be released from the cut-out portion 90.

Figure 5:
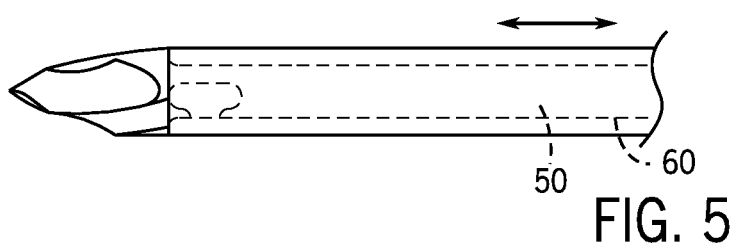
FIG. 5 depicts a side view of the combination drill bit and grasping instrument in one embodiment, showing the interior of the drill bit body in the closed orientation.

When the surgeon wishes to use the device as a drill, the surgeon returns the body portion 40 to the closed orientation of FIGS. 1 and 5 so that the shaft 60 (with the cut-out portion 90) is completely covered by the body portion 40 of the drill bit 1 (as shown in FIGS. 1 and 5). In this orientation, the drill bit 1 may only then be allowed to rotate and the drill bit 1 may act as a standard surgeon drill. As a result, a single tool can be used to both grasp and move an object 100 as well as drill within a body.

Figure 10:
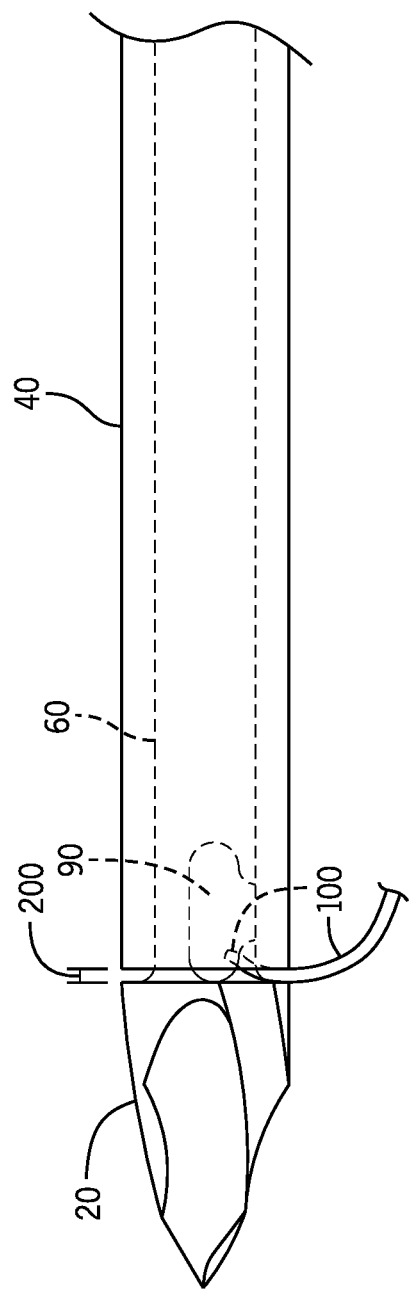
FIG. 10 illustrates the instrument grasping an object.

Referring now to FIGS. 8-10, in an embodiment, the object 100 may be grasped by the instrument so that a portion of the object 100 (if the object is flexible) may be partially located within the body portion 40 and may be compressed within a small gap 200 crated between the head portion 20 and the body portion 40 as shown in FIG. 10. A spring 300 connected to the trigger 190 may be biased and may force the body portion 40 forward so that the first end 41 of the body portion 40 presses against the head portion 20 in the relaxed state. As a result, the spring 300 provides the force to grasp the object 100. When the surgeon pulls the trigger 190 toward the handle 180, the spring 300 is compressed within a channel 310 and the body 40 moves toward the handle 180 exposing the cut-out portion 90 of the shaft 60. When the pressure on the trigger 190 is released, the body 40 moves forward again to contact the head portion 20 and the cut-out portion 90 of the shaft 60 is again concealed as in FIG. 1.

While all of the fundamental characteristics and features of the combination drill bit and grasping device herein, have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention.

The present device may also be used in non-orthopedic surgeries and even in non-medical procures as diverse as, for example, automotive repair. Consequently, all such modifications and variations and substitutions are considered included within the scope of the invention as defined by the following claims.

I claim:

1. A combination surgical drill and remote grasping device comprising:
   a handle portion;
   a first unit having a first end, a second end and a shaft portion, wherein the first end of the first unit is a drill bit;
   a second unit having a first end and a second end and an interior channel;
   wherein the shaft portion of the first unit has an opening forming a hook having a first extended lip and a second extended lip; and
   wherein the second unit may move with respect to the first unit from a first position to a second position, wherein the hook of the shaft of the first unit is concealed within the second unit while in the first position but wherein the hook of the shaft is at least partially exposed in the second position.

2. The combination surgical drill and remote grasping device of claim 1 wherein the drill bit of the first unit rotates three hundred and sixty degrees along an axis.

3. The combination surgical drill and remote grasping device of claim 1 wherein the interior channel of the second unit is not cylindrical.

4. The combination surgical drill and remote grasping device of claim 1 wherein the second unit is flexible.

5. The combination surgical drill and remote grasping device of claim 1 further comprising:
   a first edge and a second edge of the opening of the hook.

6. The combination surgical drill and remote grasping device of claim 1 further comprising:
   a spring located within the handle, wherein the spring forces the second unit toward the first unit.

7. The combination surgical drill and remote grasping device of claim 1 further comprising:
   a motor located within the handle, wherein the motor rotates the first unit.

8. The combination surgical drill and remote grasping device of claim 1 wherein the first end of the first unit remains at a constant distance from the handle portion while the second unit may move along an axis from a first position to a second position with respect to the handle unit.

9. The combination surgical drill and remote grasping device of claim 1 wherein the first unit is made from a non-corrosive metal.

10. The combination surgical drill and remote grasping device of claim 1 wherein the first unit is prevented from rotating while the second unit is moved in the second position and wherein the hook of the shaft of the first unit is exposed.

* * * * *